(12) United States Patent
Madson (10) Patent No.: US 8,685,355 B2
(45) Date of Patent: Apr. 1, 2014

(54) MANUFACTURING OF MEOH, FORMALDEHYDE, FORMIC ACID AND AMMONIUM PENTABORATE TETRAHYDRATE FROM CO2

(75) Inventor: Michael A. Madson, Garner, IA (US)

(73) Assignee: Biologistics LLC, Garner, IA (US)

( * ) Notice: Subject to any disclaimer, the term of this patent is extended or adjusted under 35 U.S.C. 154(b) by 142 days.

(21) Appl. No.: 13/430,837

(22) Filed: Mar. 27, 2012

(65) Prior Publication Data

US 2013/0053602 A1    Feb. 28, 2013

Related U.S. Application Data

(60) Provisional application No. 61/527,194, filed on Aug. 25, 2011.

(51) Int. Cl.
| | |
|---|---|
| *C01B 35/14* | (2006.01) |
| *C07C 53/02* | (2006.01) |
| *C07C 45/41* | (2006.01) |
| *C07C 29/15* | (2006.01) |

(52) U.S. Cl.
USPC ............ 423/279; 562/609; 568/484; 568/880

(58) Field of Classification Search
CPC ........ C01B 35/10; C07C 53/02; C07C 45/41; C07C 47/04
See application file for complete search history.

(56) References Cited

U.S. PATENT DOCUMENTS 2,872,474 A * 2/1959 Pearson et al. ................ 558/295

OTHER PUBLICATIONS

Monhanazadeh et al (Monatshefte für Chemie, Sodium Borohydride—Ammonium Carbonate: An Effective Reducing System for Aldehydes and Ketones, 2005, 136, pp. 2041-2043.*
Zheng Shen, Yalei Zhang and Fangming Jin; Hydrothermal Transfer Hydrogenation of NaHCO3 into Formate by Isopropanol; symposium; Mar. 25, 2012; 1 page; CO2 Capture, Sequestration, Conversion and Utilization; San Diego, California.
S.G. Prakash; Beyond Oil and Gas: The Methanol Economy; symposium; Mar. 28, 2012; 1 page; CO2 Capture, Sequestration, Conversion and Utilization; San Diego, California.
Siti Nurhanna Riduan, Yugen Zhang and Jackie Y. Ying; Conversion of Carbon Dioxide into Methanol with Silanes over N-Hetrocyclic Carbene Catalysts; journal; 2009; pp. 3322-3325; vol. 48; Wiley-VCH Verlag GmgH & Co. KGaA, Weinheim, Germany.

* cited by examiner

*Primary Examiner* — Paul A Zucker
(74) *Attorney, Agent, or Firm* — Zarley Law Firm, P.L.C.

(57) ABSTRACT

A method of forming methanol, formaldehyde, formic acid and ammonium pentaborate tetrahydrate includes the steps of providing ammonium hydroxide and producing air bubbles within the ammonium hydroxide to form a solution. Sodium borohydride is added and dissolved within the solution of air bubbled ammonium hydroxide to form methanol, formaldehyde, formic acid and ammonium pentaborate tetrahydrate. An alternative method of forming methanol, formaldehyde, formic acid and ammonium pentaborate tetrahydrate is also provided which includes the steps of providing ammonium hydroxide and dissolving sodium borohydride therein to form a solution. Sodium bicarbonate is added to the solution of ammonium hydroxide and sodium borohydride to form methanol, formaldehyde, formic acid and ammonium pentaborate tetrahydrate.

11 Claims, 8 Drawing Sheets

| Compound | Solubility | Melting Point |
|---|---|---|
| Ammonium formate | 102 g/100 ml | 116 °C |
| Ammonium pentaborate tetrahydrate | 10.9 g/100 ml | 110 °C – $H_2O$ |
| Ammonium bicarbonate | 11.9 g/100 ml | 107 °C |
| Ammonium carbonate | 100 g/100 ml | 258 °C |
| Sodium formate | – | 253 °C |
| Sodium borate | – | 75 °C |
| Sodium bicarbonate | – | 270 °C – $CO_2$ |
| Sodium carbonate hydrate | – | 100 °C – $H_2O$ |

MANUFACTURING OF MEOH, FORMALDEHYDE, FORMIC ACID AND AMMONIUM PENTABORATE TETRAHYDRATE FROM CO2

CROSS REFERENCE TO RELATED APPLICATIONS

This application claims the benefit of U.S. Provisional Application No. 61/527,194, filed Aug. 25, 2011.

BACKGROUND OF THE INVENTION

This invention relates to a method for manufacturing methanol, formaldehyde, formic acid and ammonium pentaborate tetrahydrate. More specifically, this invention relates to reducing carbon dioxide in order to form methanol, formaldehyde, formic acid and ammonium pentaborate tetrahydrate.

Methanol is an alcohol with a chemical formula $CH_3OH$ and is the simplest alcohol that is utilized in producing biodiesel, antifreeze, solvents, fuel and the like. Typically, in order to manufacture methanol natural gas must be utilized or alternatively, coal, presenting a chemical reaction that emits harmful greenhouse gases that help fuel global warming. In addition, there are great costs associated with producing methanol and utilizing it in biodiesel type environments. Thus, a need in the art exists for a cost effective alternative way of manufacturing methanol as well as providing the product streams formaldehyde, formic acid and ammonium pentaborate tetrahydrate that would also reduce greenhouse gasses by their production and consumption.

In 2009, 20,000 tons of formic acid were produced. One method of production is to add carbon monoxide to methanol to form methyl formate. Estimated annual production of formaldehyde in 2005 was 50 billion pounds. It is mostly produced by the catalytic oxidation of methanol. Catalysts used are silver metal or a mixture of iron and molybdenum or vanadium oxides. The fourth product from this reaction is ammonium pentaborate tetrahydrate. Its uses are; 1. electrolytic capacitors; 2. corrosion inhibitors; 3. welding; and 4. flame retardants.

SUMMARY OF THE INVENTION

A method of forming methanol, formaldehyde, formic acid and ammonium pentaborate tetrahydrate. The method includes the steps of providing ammonium hydroxide and producing air bubbles within the ammonium hydroxide to form a solution. Sodium borohydride is added and dissolved within the solution of air bubbled ammonium hydroxide to form methanol formaldehyde, formic acid and ammonium pentaborate tetraydrate. An alternative method of forming methanol, formaldehyde, formic acid and ammonium pentaborate tetrahydrate is also disclosed. The alternative method includes the steps of providing ammonium hydroxide and dissolving sodium borohydride therein to form a solution. Sodium bicarbonate is added to the solution of ammonium hydroxide and sodium borohydride to form methanol, formaldehyde, formic acid and ammonium pentaborate tetrahydrate.

DESCRIPTION OF THE PREFERRED EMBODIMENT

The graphs and figures present a method of manufacturing methanol, formaldehyde, formic acid and ammonium pentaborate tetrahydrate by reducing carbon dioxide ($CO_2$) through multiple chemical reactions. In a preferred method a container is provided with 1 N $NH_4OH$, 1 N ammonium hydroxide where a tube element provides air bubbles within the 1 N ammonium hydroxide. At this point sodium borohydride $BH_4$ is added and dissolved within the solution of air bubbled 1 N ammonium hydroxide in order to form methanol, formaldehyde, formic acid and ammonium pentaborate tetrahydrate. In an alternative method the container contains 1 N ammonium hydroxide (1 N $NH_4OH$) and sodium borohydride (NABH4) is dissolved therein at which point in time sodium bicarbonate $NaHCO_3$ is added to the solution to form methanol, formaldehyde, formic acid and ammonium pentaborate tetrahydrate. Thus, using both methods all four products are manufactured.

Shown below is the IR Spectral Absorption and Assignments showing the chemical reactions as discussed.

| IR Spectral Absorptions and Assignments for Carbon Dioxide Reduction | | |
|---|---|---|
| Methanol Standard | Bubbled Air Reaction Extract | $NaHCO_3$ Reaction Extract |
| 640 $cm^{-1}$ | 680 $cm^{-1}$ formaldehyde | 685 $cm^{-1}$ formaldehyde |
| 1160 $cm^{-1}$ methanol | 1170 $cm^{-1}$ methanol | 1170 $cm^{-1}$ methanol |
|  | 1210 $cm^{-1}$ formaldehyde | 1215 $cm^{-1}$ formaldehyde |
|  | 1310 $cm^{-1}$ formaldehyde | 1310 $cm^{-1}$ formaldehyde |

-continued

IR Spectral Absorptions and Assignments for Carbon Dioxide Reduction

| Methanol Standard | Bubbled Air Reaction Extract | NaHCO$_3$ Reaction Extract |
|---|---|---|
| | 1360 cm$^{-1}$ sodium formate | 1370 cm$^{-1}$ sodium formate |
| | 1655 cm$^{-1}$ formaldehyde | 1650 cm$^{-1}$ formaldehyde |
| | 2890 cm$^{-1}$ formic acid | 2890 cm$^{-1}$ formic acid |
| | 2940 cm$^{-1}$ formic acid | 2940 cm$^{-1}$ formic acid |
| 2560-3480 cm$^{-1}$ methanol | 3290-3490 cm$^{-1}$ methanol | 3000-3570 cm$^{-1}$ methanol |

Peak assignments were deduced from standard IR spectra.

Thus, when the 1 N ammonium hydroxide with bubbled air is dissolved in the borohydride no boric acid or B—H is present in the reaction mixture extract. Specifically, from the results B—H stretch is infrared absorbance range of 2500 cm$^{-1}$ to 2600 cm$^{-1}$. There is no B—H stretch absorbance in this region for the reaction mixture extract of methanol, formaldehyde, formic acid and ammonium pentaborate tetrahydrate for both embodiments discussed above. Specifically, boric acid has absorbance in the infrared at two sets of two concomitant peaks. They are 1150 cm$^{-1}$ and 1410 cm$^{-1}$ and secondly 945 cm$^{-1}$ and 1150 cm$^{-1}$. Although 1150 cm$^{-1}$ is close in value to the 1170 cm$^{-1}$ value found in the two spectra as depicted above, in the reactions there is no concomitant peak for 1150 cm$^{-1}$, 1410 cm$^{-1}$, and there is no concomitant peak for 1150 cm$^{-1}$, 945 cm$^{-1}$. Consequently, there is no boric acid in the mixture wherein the methanol, formaldehyde, formic acid and ammonium pentaborate tetrahydrate are extracted. Specifically, the infrared peak of 1170 cm$^{-1}$ from the sample is the methanol itself.

Figure 1:
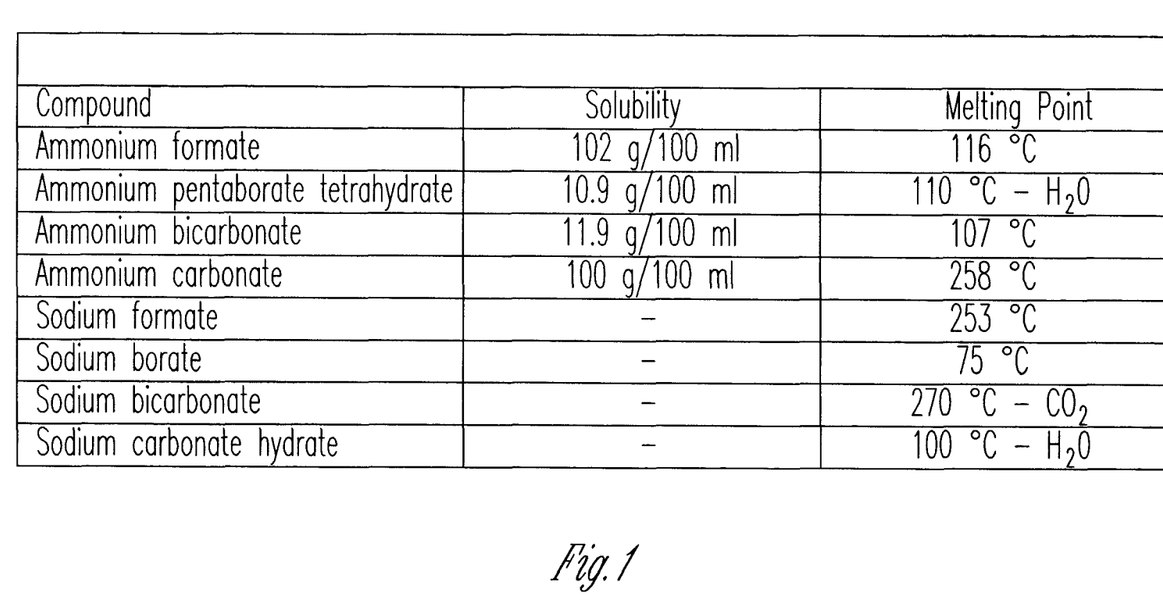
FIG. 1 is a table of the possible identities of a crystalline solid produced as a product of a hydride insertion reaction of the present method.

We find formic acid or sodium formate at 1360 cm$^{-1}$, 2890 cm$^{-1}$ and 2940 cm$^{-1}$ in the IR spectrum for both methods of preparation of methanol, formaldehyde, formic acid and ammonium pentaborate tetrahydrate. We find formaldehde IR peaks at 680 cm$^{-1}$, 1210 cm$^{-1}$, 1310 cm$^{-1}$ and 1650 cm$^{-1}$ for both methods of preparation. Finally we find IR peaks for methanol at 1170 cm$^{-1}$ and 3000 cm$^{-1}$-3590 cm$^{-1}$ for both methods of preparation. Instead of boric acid or B—H a product of the hydride is ammonium pentaborate tetrahydrate. Specifically, in the reaction the byproduct had a loss of water/melting point between 104-106° C. wherein literature reports the loss of water point is at 110° C. Specifically, if the reaction volume of water is kept to half the reaction value previously used, then the ammonium pentaborate tetrahydrate crystallizes out and its solubility is 10.9 g/100 ml of water. The ammonium pentaborate tetrahydrate was isolated by pouring off the reaction volume, washing the ammonium pentaborate tetrahydrate with less than 0.5 mL of ammonium hydroxide, drying, and subsequently determining the loss of water point. Additional findings relevant to the loss of water/melting point between 104-106° C. of the reaction the byproduct were that the sample did not melt at this temperature, but instead loses liquid, which is presumably water. This further indicates that the material crystallizing immediately is ammonium pentaborate tetrahydrate. Additionally, when the temperature was increased to 150° C., the sample still did not melt. The data provided in the table of FIG. 1 is additionally illustrative of the foregoing findings.

Figure 2:
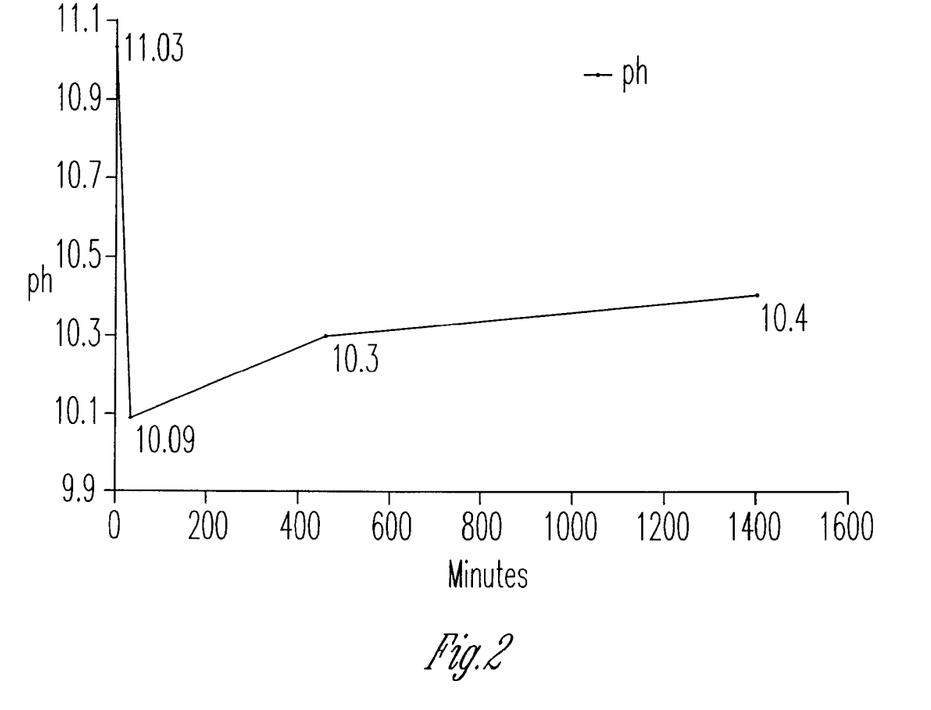
FIG. 2 is a graph of the pH of the reaction mixture of the reduction of sodium bicarbonate to methanol versus time.

The calculated yield of ammonium pentaborate tetrahydrate from hydride reduction of sodium bicarbonate is is 1099.5 mg. With solubility of 10.9 g/100 ml, the soluble quantity of ammonium pentaborate tetrahydrate is 436 mg in this reaction mixture. Subtracting the soluble yield from the predicted yield gives 663.5 mg. 692 mg of the compound was isolated, which represents a difference of 4% from that which was calculated as 100% of crystallized yield, which is 663.5 mg. This implied that sodium borohydride is completely converted to borate in the reaction. Because this is a strongly basic reaction mixture there is no acid that would decompose borohydride to boric acid, as shown in FIG. 2. As a result, there is no acid in the reaction mixture that would decompose borohydryde to boric acid; this suggests that something is reduced, most likely ammonium carbonate to the methanol, formaldehyde, formic acid and ammonium pentaborate tetrahydrate.

A mechanism for the synthesis of methanol from carbon dioxide, 1-N NH$_4$OH and NaBH$_4$ is shown. Three sodium bicarbonate reductions and one air bubbled ammonium hydroxide solution reduction is thus presented where both reaction conditions produce methanol, formaldehyde and formic acid. The above mechanism of carbon dioxide reduction for the synthesis of methanol from carbon dioxide, 1-N NH$_4$OH and NaBH$_4$, illustrates one sodium bicarbonate reduction and one air bubbled ammonium hydroxide solution reduction. Both reaction conditions produce methanol, formic acid, and formaldehyde. In base the occurrence of protons is minimal, so the existence of a proton, to facilitate the evolution of water, is presumably accomplished by the weak Bronsted acid, the ammonium ion. Thus, five molecules of ammonium ion are evolved as ammonia for each molecule of methanol, and vigorous bubbling occurs during the reaction.

Figure 3:
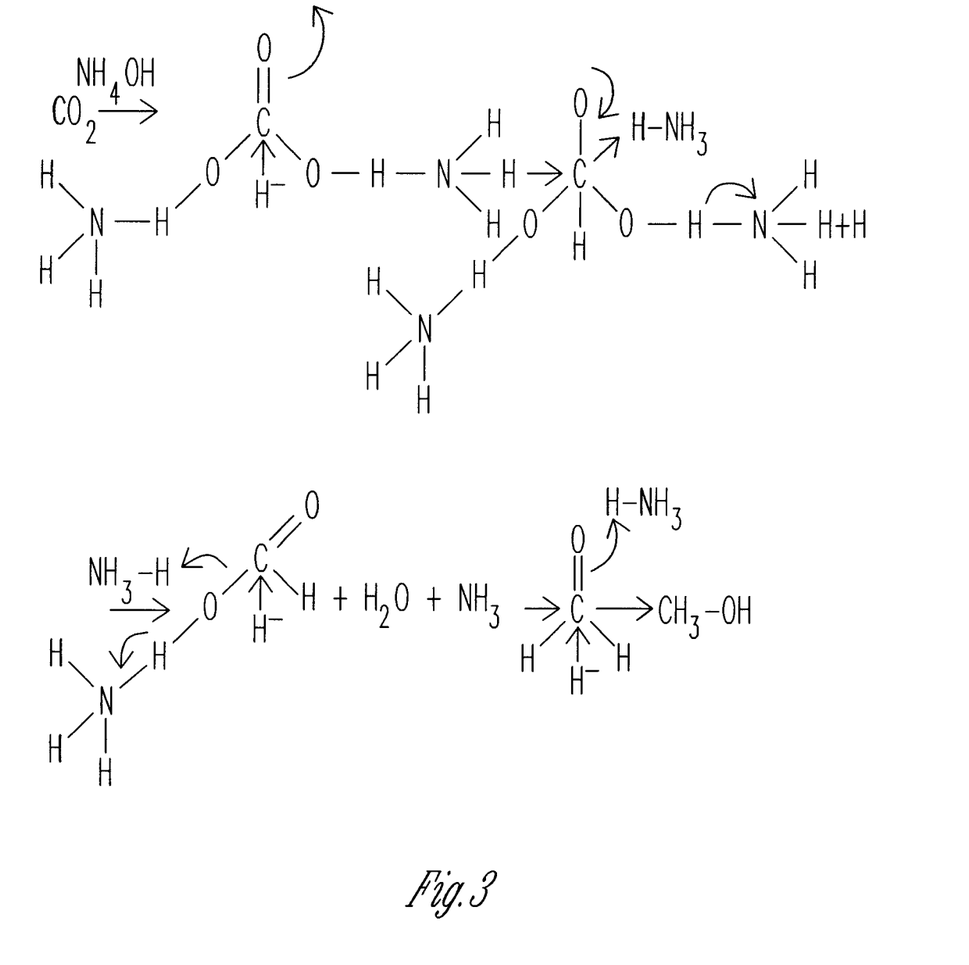
FIG. 3 is a diagram of a molecular structure that is the mechanism of a reaction.

The mechanism of the reduction of ammonium carbonate, sequestered by bubbling air through a 1 normal solution of ammonium hydroxide with sodium borohydride is shown to produce above, FIG. 3, to produce methanol, formaldehyde and formic acid. This is the same hydride insertion/reduction that is the basis for aqueous sulfate phosphate discernment.

Specifically, the ammonium salts of the ions in the reduction of carbon dioxide to methanol are a key element. They provide partial covalent bonding from the carbonic acid through the ammonium ion proton and the nitrogen of the carbonic acid salt. This means there would be more positive charge on the carbonyl carbon of carbonic acid. They also provide an ion that can regenerate the free acid simply by the loss of a proton and evolution of ammonia gas. The latter function can also be important in the loss of water, the attack of carbon bound hydroxyl group to the ammonium ion proton, and the loss of ammonia gas and water. This elimination of water and evolution of ammonia gas can serve to drive the whole reaction forward.

There is additional evidence that supports this hydride insertion reaction. The hydride insertion protocol can be used to discern the structures of possible carbohydrate sulfate/phosphate esters. As an example, a hydride insertion can be taken to a possible sulfate ester and compared to a hydride insertion to a possible phosphate ester of a major κ casein O-linked oligosaccharide alditols, wherein m/z 966.1 is molecular weight −1 amu for N-Acetyl-neuraminyl$_2$-Gal-GlcNHAc—OH noted by Saito and Itoh. (T. Saito and T. Itoh. Variations and distributions of O-glycosidically linked sugar chains in bovine κ casein. J. Dairy Science 1992 75 1768-1775). There is a difference of 2 amu for singly charged ions and a difference of 1 amu for doubly charged ions for phosphate/sulfate esters. The ion found in the spectrum is compared to the two calculated ions and based upon the comparison, the two esters can be discerned. The sulfate esters of κ casein O-linked oligosaccharide alditols are provided. Thus, this is an example of hydride insertion reduction of oxyanions, much like the hydride reduction of the oxyanion ammonium carbonate to formic acid, formaldehyde, and methanol and supports the hydride reduction of ammonium carbonate to methanol, formaldehyde, formic acid and ammonium pentaborate tetrahydrate.

Figure 4:
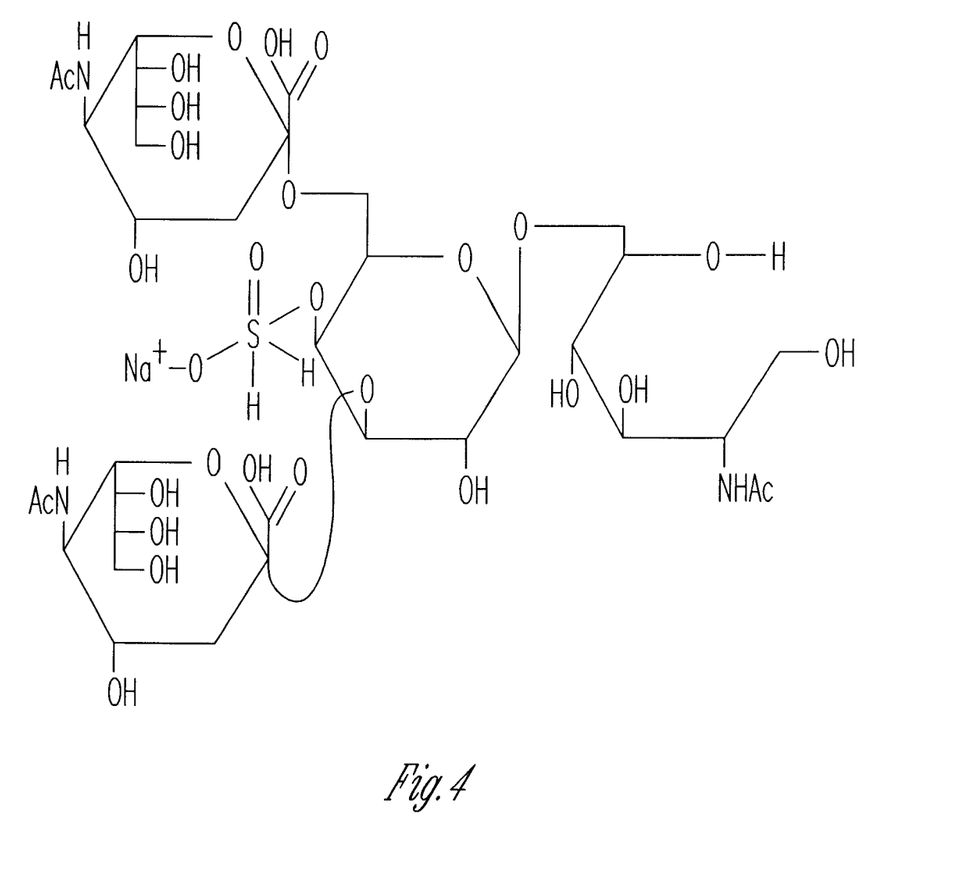
FIG. 4 is a diagram of the probable molecular structure of the ion found at m/z 1055.1 which is sulfated and reduced after the removal by beta-elimination of the O-linked oligosaccharide from κ casein and reduction using pH 11.4 $NH_4OH$ and $NaBH_4$.
Figure 5:
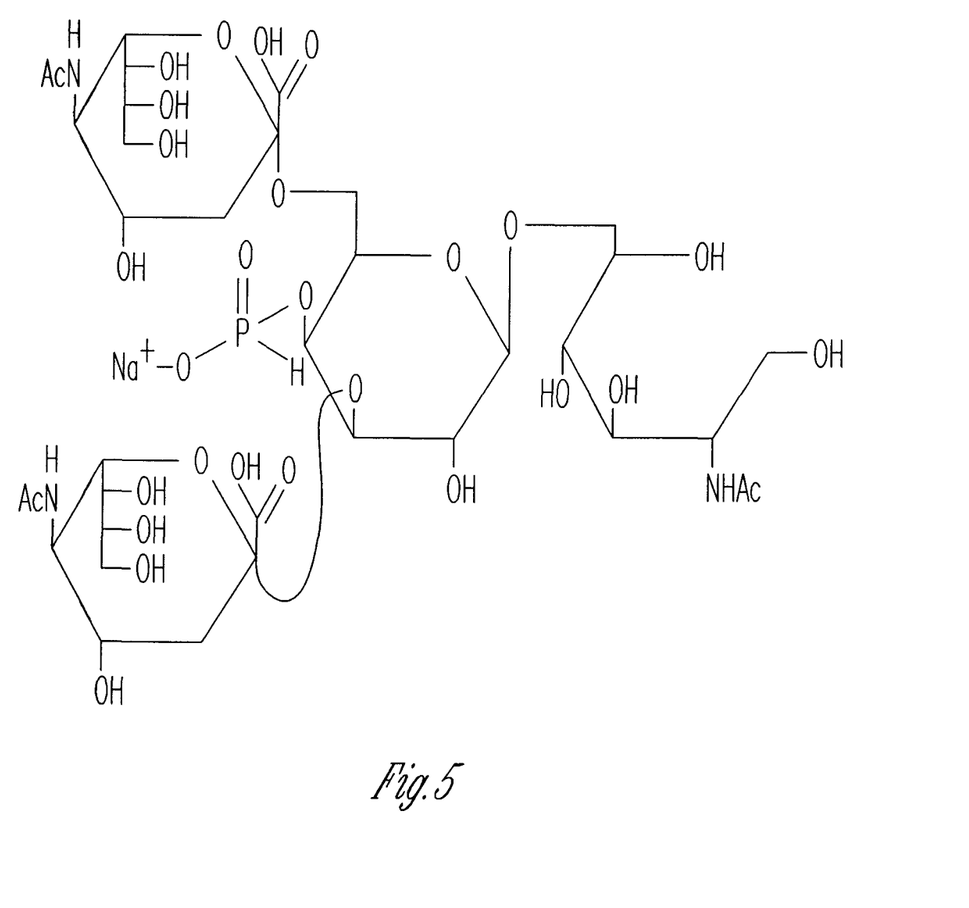
FIG. 5 is a diagram of a molecular structure of a phosphorylated and reduced, molecule.

With reference to FIG. 3, not found in Saito and Itoh's report on κ casein O-linked oligosaccharides is the ion illustrated in FIG. 4, m/z 1055.1. It is proposed that this molecule is sulfated and reduced after the removal by beta-elimination of the O-linked oligosaccharide from κ casein and reduction using pH 11.4 $NH_4OH$ and $NaBH_4$. The structure shown also supports the hydride reduction of $CO_2$ to methanol, formaldehyde, formic acid and ammonium pentaborate tetrahydrate. Furthermore, by comparing the phosphorylated and reduced molecule illustrated in FIG. 5 to the molecule shown in FIG. 4 (the sulfated molecule), it was found that the sulfated molecule is more reasonable. The example provided in FIG. 5 of a reduced, sulfated molecule is shown to support the hydride insertion reaction discernment of phosphate/sulfate esters of carbohydrates, and also supports hydride reduction of $CO_2$ to methanol formaldehyde, formic acid and ammonium pentaborate tetrahydrate.

Figure 6A:
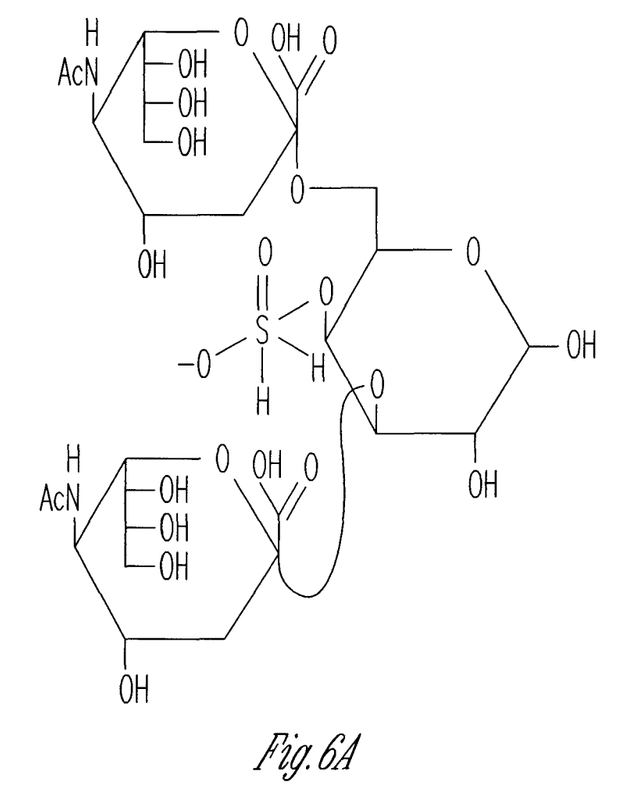
FIG. 6A is a diagram of the molecular structure of ions which are the probable hydrolysis products from the reduced mono- or di-sulfated/phosphorylated O-linked oligosaccharide beta eliminated from κ casein.
Figure 6B:
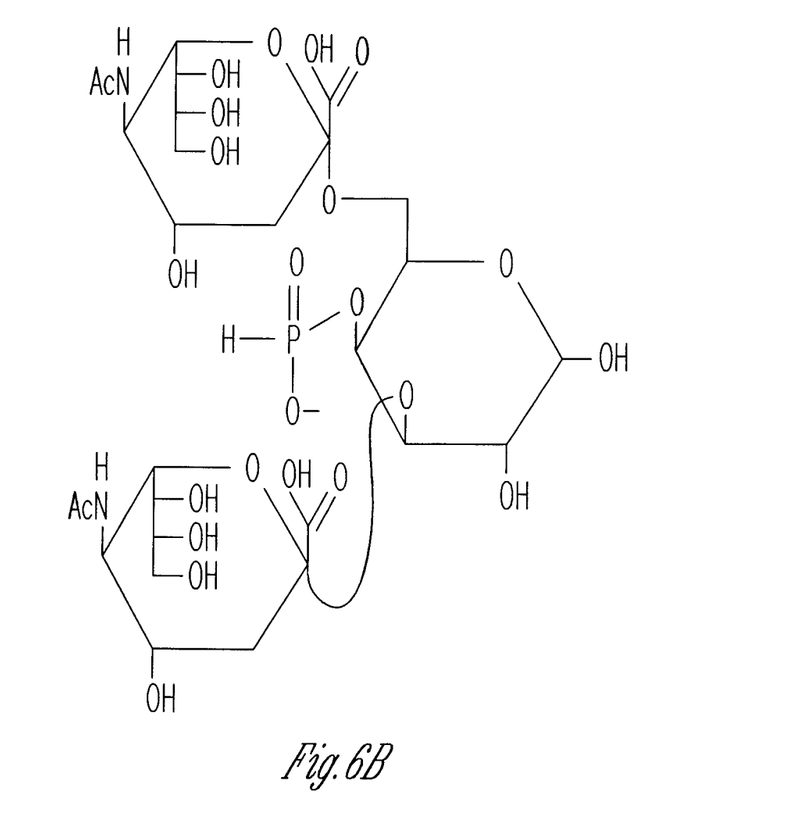
FIG. 6B is a continuation of FIG. 6A and is a diagram of the molecular structure of ions which are the probable hydrolysis products from the reduced mono- or di-sulfated/phosphorylated O-linked oligosaccharide beta eliminated from κ casein.
Figure 7:
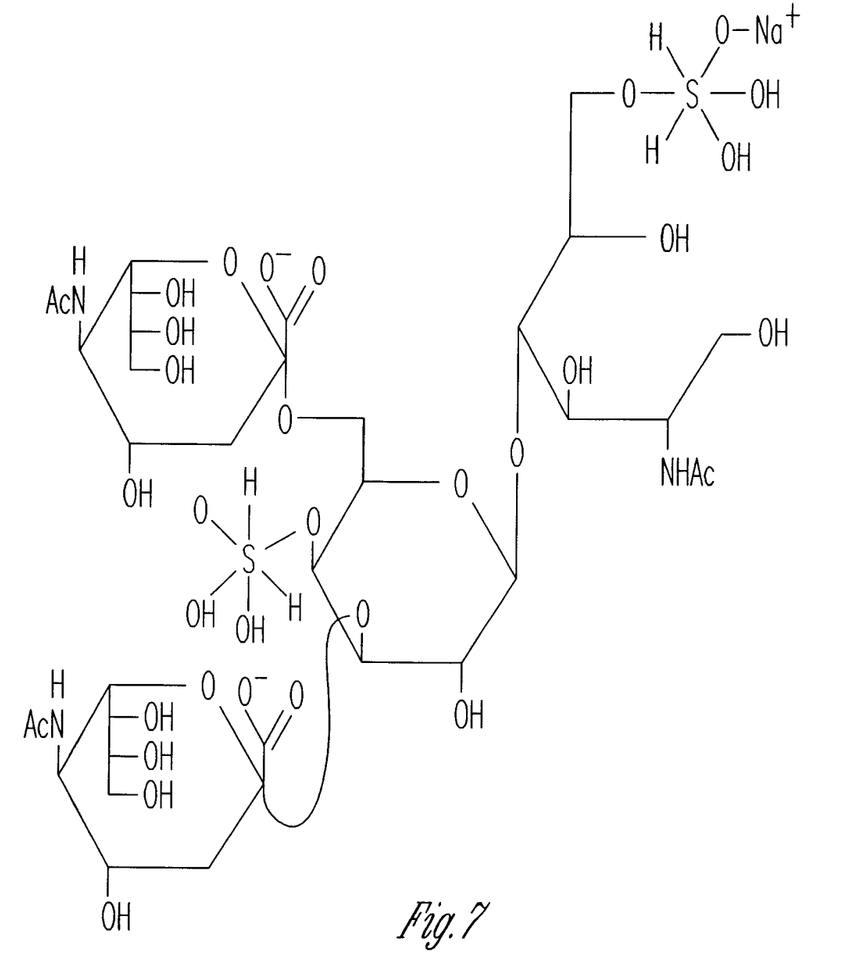
FIG. 7 is a diagram of the molecular structure illustrative of the probable identity of m/z 565.3, a dianion of the doubly reduced disulfate ester.

FIG. 6A-6B depicts the probable hydrolysis product from the reduced mono- or di-sulfated/phosphorylated O-linked oligosaccharide beta eliminated from κ casein. Ion (A) shows a difference between calculated and found readings, being 0.24 parts per thousand, whereas the phosphorylated ion (B) is 2.7 parts per thousand, thus adding further support to the sulfate reduction and hydride reduction of $CO_2$ to methanol. FIG. 6C shows a mechanism of a reaction and further support for the hydride reduction of $CO_2$ to methanol, formaldehyde, formic acid and ammonium pentaborate tetrahydrate is provided in FIG. 7, which illustrates the probable identity of m/z 565.3, a dianion of the doubly reduced disulfate ester of the parent compound.

Thus, provided is a method of manufacturing methanol, formaldehyde, formic acid and ammonium pentaborate tetrahydrate from carbon dioxide. This is done by reducing carbon dioxide as a result of bubbling air through ammonium hydroxide solution and adding sodium borohydride. By utilizing this mixture large quantities of methanol, formaldehyde, formic acid and ammonium pentaborate tetrahydrate can be produced for fuel use and otherwise without the needed and unnecessary emission of greenhouse gases or the use of natural gas or coal. Thus, an efficient and inexpensive way of manufacturing methanol, formaldehyde, formic acid and ammonium pentaborate tetrahydrate from carbon dioxide is provided that is environmentally friendly, reduces greenhouse gases, and reduces global warming. Furthermore, by reducing carbon dioxide to formic acid, reducing formic acid to formaldehyde, and reducing formaldehyde to methanol, a side reaction results in the formation of ammonium pentaborate tetrahydrate, and all four of the foregoing products are valuable to the chemical industry. Thus, at the very least all of the problems of the background have been addressed.

What is claimed is:

1. A method of forming methanol, formaldehyde, formic acid and ammonium pentaborate tetrahydrate comprising the steps of:
   providing ammonium hydroxide;
   producing air bubbles within the ammonium hydroxide to form a solution;
   adding and dissolving sodium borohydride within the solution of air bubbled ammonium hydroxide;
   forming methanol, formaldehyde, formic acid and ammonium pentaborate tetrahydrate.

2. The method of forming methanol formaldehyde, formic acid and ammonium pentaborate tetrahydrate of claim 1 wherein the sodium borohydride is dissolved in the ammonium hydroxide with bubbled air such that no boric acid is produced.

3. The method of forming methanol, formaldehyde, formic acid and ammonium pentaborate tetrahydrate of claim 2 additionally comprising the step of producing ammonium pentaborate tetrahydrate as the product of a hydride.

4. The method of forming methanol, formaldehyde, formic acid and ammonium pentaborate tetrahydrate of claim 3 wherein the ammonium hydroxide is provided in a container and a tube element is introduced into the container such that the air bubbles are provided within the ammonium hydroxide.

5. The method of forming methanol, formaldehyde, formic acid and ammonium pentaborate tetrahydrate of claim 4 wherein the container is provided with 1-N ammonium hydroxide.

6. The method of forming methanol, formaldehyde, formic acid and ammonium pentaborate tetrahydrate of claim 5 wherein carbon dioxide is reduced through multiple chemical reactions.

7. A method of forming methanol, formaldehyde, formic acid and ammonium pentaborate tetrahydrate comprising the steps of:
   providing ammonium hydroxide and dissolving sodium borohydride therein to form a solution;
   adding sodium bicarbonate to the solution of ammonium hydroxide and sodium borohydride; and
   forming methanol, formaldehyde, formic acid and ammonium pentaborate tetrahydrate.

8. The method of forming methanol, formaldehyde, formic acid and ammonium pentaborate tetrahydrate of claim 7 additionally comprising the step of producing ammonium pentaborate tetrahydrate as the product of a hydride.

9. The method of forming methanol, formaldehyde, formic acid and ammonium pentaborate tetrahydrate of claim 8 wherein the ammonium hydroxide is provided in a container.

10. The method of forming methanol, formaldehyde, formic acid and ammonium pentaborate tetrahydrate of claim 9 wherein the container is provided with 1-N ammonium hydroxide.

11. The method of forming methanol, formaldehyde, formic acid and ammonium pentaborate tetrahydrate of claim 10 wherein carbon dioxide is reduced through multiple chemical reactions.

\* \* \* \* \*